US009439737B2

(12) United States Patent
Carrillo Gonzalez et al.

(10) Patent No.: US 9,439,737 B2
(45) Date of Patent: Sep. 13, 2016

(54) ORTHODONTIC INDIRECT BONDING TRAY INCLUDING STABILIZATION FEATURES

(71) Applicants: Roberto J. Carrillo Gonzalez, San Pedro Garza Garcia (MX); Roberto Carrillo Fuentevilla, San Pedro Garza Garcia (MX)

(72) Inventors: Roberto J. Carrillo Gonzalez, San Pedro Garza Garcia (MX); Roberto Carrillo Fuentevilla, San Pedro Garza Garcia (MX)

( * ) Notice: Subject to any disclaimer, the term of this patent is extended or adjusted under 35 U.S.C. 154(b) by 0 days.

(21) Appl. No.: 14/302,005

(22) Filed: Jun. 11, 2014

(65) Prior Publication Data
US 2015/0359610 A1    Dec. 17, 2015

(51) Int. Cl.
*A61C 3/00*  (2006.01)
*A61C 7/14*  (2006.01)

(52) U.S. Cl.
CPC .................... *A61C 7/146* (2013.01)

(58) Field of Classification Search
CPC ........... A61C 7/146; A61C 7/00; A61C 7/02
USPC .................................. 433/3, 6, 24
See application file for complete search history.

(56) References Cited

U.S. PATENT DOCUMENTS

| 4,526,540 | A | * | 7/1985 | Dellinger ............... A61C 7/146 433/24 |
| 6,918,761 | B2 | * | 7/2005 | Sachdeva ................ A61C 7/00 433/24 |
| 7,188,421 | B2 | * | 3/2007 | Cleary et al. ..................... 433/8 |
| 7,556,496 | B2 | | 7/2009 | Cinader et al. |
| 7,762,815 | B2 | | 7/2010 | Cinader et al. |
| 7,845,938 | B2 | | 12/2010 | Kim et al. |
| 7,878,806 | B2 | | 2/2011 | Lemchen |
| 8,070,486 | B2 | | 12/2011 | Kuperman |
| 8,308,478 | B2 | | 11/2012 | Primus et al. |
| 2010/0279243 | A1 | * | 11/2010 | Cinader et al. ................... 433/3 |

* cited by examiner

*Primary Examiner* — Heidi M Eide
(74) *Attorney, Agent, or Firm* — Elizabeth Philip Dahm; Kelly J. Kubasta; Ferguson, Braswell & Fraser, PC

(57) ABSTRACT

A tray for use in bonding orthodontic appliances to selected teeth of a patient is disclosed. The tray includes an outer shell having wall sections extending over facial, lingual, and occlusal surfaces of the selected teeth to form a channel including tooth cavities having a configuration matching and arranged for receiving the selected teeth. A matrix is bonded to the inner surface of the outer shell and is contoured to complement the facial or lingual surface of the teeth. A stabilization member extends from the outer shell and includes an inside surface contoured to complement at least a portion of the facial surface of a tooth located adjacent the selected teeth. Orthodontic appliances are detachably connected to the matrix, wherein each appliance includes a base for bonding the appliance to a tooth.

19 Claims, 3 Drawing Sheets

ORTHODONTIC INDIRECT BONDING TRAY INCLUDING STABILIZATION FEATURES

FIELD OF THE INVENTION

This invention relates to method and apparatus for bonding orthodontic appliances such as brackets to a patient's teeth. The present invention specifically relates to an indirect bonding tray including stabilization features.

BACKGROUND OF THE INVENTION

Orthodontic treatment involves movement of malpositioned teeth to desired locations in the oral cavity. Orthodontic treatment can improve the patient's facial appearance, especially in instances where the teeth are noticeably crooked or where the jaws are out of alignment with each other. Orthodontic treatment can also enhance the function of the teeth by providing better occlusion during mastication.

One common type of orthodontic treatment involves the use of tiny, slotted appliances known as brackets. The brackets are fixed to the patient's teeth and an arch wire is placed in the slot of each bracket. The arch wire forms a track to guide movement of teeth to desired locations.

The ends of orthodontic arch wires are often connected to small appliances known as buccal tubes that are, in turn, secured to the patient's molar teeth. In many instances, a set of brackets, buccal tubes and an arch wire is provided for each of the patient's upper and lower dental arches. The brackets, buccal tubes and arch wires are commonly referred to collectively as "braces".

In many types of orthodontic techniques, the precise position of the appliances on the teeth is an important factor for helping to ensure that the teeth move to their intended final positions. In general, orthodontic appliances that are adapted to be adhesively bonded to the patient's teeth are placed and connected to the teeth by either one of two techniques: a direct bonding technique, or an indirect bonding technique.

In the direct bonding technique, the appliance and adhesive are grasped with a pair of tweezers or other hand instrument and placed by the practitioner on the surface of the tooth in an approximate desired location. Next, the appliance is shifted along the surface of the tooth as needed until the practitioner is satisfied with its position. Once the appliance is in its precise, intended location, the appliance is pressed firmly onto the tooth to seat the appliance in the adhesive. Excess adhesive in areas adjacent the base of the appliance is removed, and the adhesive is then allowed to cure and fix the appliance firmly in place. While the direct bonding technique described above is in widespread use and is considered satisfactory by many, there are shortcomings that are inherent with this technique. For example, access to surfaces of malposed teeth may be difficult. In some instances, and particularly in connection with posterior teeth, the practitioner may have difficulty seeing the precise position of the bracket relative to the tooth surface. Additionally, the appliance may be unintentionally dislodged from its intended location during the time that the excess adhesive is being removed adjacent the base of the appliance.

Indirect bonding techniques avoid many of the problems associated with direct bonding. In general, indirect bonding techniques known in the past have involved the use of a placement device or transfer apparatus having a shape that matches the configuration of one or more of the patient's teeth in the dental arch. One type of placement device or transfer apparatus is often called a "transfer tray" and typically has a cavity for receiving a number of teeth simultaneously. A set of appliances such as brackets are releasably connected to the tray at certain, predetermined locations.

During the use of an orthodontic transfer apparatus for indirect bonding, an adhesive is typically applied to the base of each appliance by the orthodontist or a staff member. The device is then placed over the patient's teeth and remains in place until such time as the adhesive hardens. Next, the apparatus is detached from the teeth as well as from the appliances, with the result that all of the appliances previously connected to the apparatus are now bonded to respective teeth at their intended, predetermined locations.

In more detail, one method of indirect bonding of orthodontic appliances using the transfer tray described above includes the steps of taking an impression of each of the patient's dental arches and then making a replica plaster or "stone" model from each impression. Next, the appliances are bonded to the stone models at desired locations. Optionally, the brackets may be adhesive precoated brackets.

The transfer tray is then made by placing a matrix material over the model as well as over the appliances placed in the model. For example, a plastic sheet matrix material may be held by a frame and exposed to radiant heat. Once the plastic sheet material has softened, it is placed over the model and the appliances. Air in the space between the sheet material and the model is then evacuated, and the plastic sheet material assumes a configuration that precisely matches the shape of the replica teeth of the stone model and attached appliances. The plastic sheet matrix material is then allowed to cool and harden to form a tray. The tray and the appliances (which are embedded in an interior wall of the tray) are then detached from the stone model. If the cured adhesive that was used to bond the appliances to the stone model remains on the base of the appliances after detachment from the stone model, the adhesive serves as a "custom" base having a concave contour that precisely replicates the convex contour of the previous attachment location of the stone model, as well as the convex configuration of the intended mounting location of the appliances on the patient's teeth.

Once the patient has returned to the practitioner's office, a quantity of adhesive is placed on the base of each appliance, and the tray with the embedded appliances is then placed over the matching portions of the patient's dental arch. Since the configuration of the interior of the tray closely matches the respective portions of the patient's dental arch, each appliance is ultimately positioned on the patient's teeth at precisely the same location that corresponds to the previous location of the same appliance on the stone model.

Indirect bonding techniques offer a number of advantages over direct bonding techniques. For one thing, and as indicated above, it is possible to bond a plurality of appliances to a patient's dental arch simultaneously, thereby avoiding the need to bond each appliance in individual fashion. In addition, the transfer apparatus helps to locate the appliances in their proper, intended positions such that adjustment of each appliance on the surface of the tooth before bonding is avoided. The increased placement accuracy of the appliances that is often afforded by indirect bonding techniques helps ensure that the patient's teeth are moved to their proper, intended positions at the conclusion of treatment.

In recent years, many improvements have been made in the field of indirect bonding. However, there is a continuing need in the art to improve methods for fabricating the transfer apparatus or transfer tray. For example, improper fit of the transfer tray over the patient's teeth is a common problem. For example, when a practitioner utilizes an indirect bonding technique, it is critical that the practitioner be able to precisely place the transfer tray over matching surfaces of the patient's teeth. An improperly fitted transfer tray may result in appliances being bonded to locations on the patient's teeth that are imprecise and do not correspond to the previous location of the same appliance on the stone model. As a result, malpositioned teeth may move to unintended positions during the treatment program.

Although the transfer tray is fabricated to match the surfaces of the patient's teeth, as is often the case, the transfer tray may be somewhat unstable, loose, or inaccurate. Such instability can result from several factors. For example, inaccuracies may arise during the steps leading up to the fabrication of the transfer tray. Inaccuracies may arise during fabrication of the impression of the patient's teeth, or during the fabrication of the stone model based upon each impression. Inaccuracies may also arise during bonding of the appliances to the stone model at desired locations. Additionally, inaccuracies may arise due to the fact that the transfer tray is customarily fabricated of a material that is insufficiently rigid. Due to any one or a combination of the foregoing factors, a certain amount of instability, "wiggle", or "play" often arises when the transfer tray is placed over matching surfaces of the patient's teeth during the indirect bonding process. The potential for such instability increases, especially when the transfer tray is arranged for placement over only a small number of teeth, e.g., two or three teeth.

For the foregoing reasons, it is desirable to increase placement accuracy of the transfer tray over matching surfaces of the patient's teeth during the indirect bonding procedure. It would be desirable to provide a transfer tray that includes a feature or mechanism that would provide stabilization and enable the practitioner to visually assess or determine whether the transfer tray has been placed or seated onto the patient's teeth in the position as originally planned and intended. Other than its surfaces that match a patient's teeth, currently available transfer trays (made for one or multiple teeth) do not provide the practitioner with such a feature or mechanism.

SUMMARY OF THE INVENTION

A tray for use in bonding orthodontic appliances to selected teeth of a patient is disclosed. The tray includes an outer shell having wall sections extending over facial, lingual, and occlusal surfaces of the selected teeth to form a channel including tooth cavities having a configuration matching and arranged for receiving the selected teeth. A matrix is bonded to the inner surface of the outer shell and has an inner surface, a portion of which is contoured to complement the facial surface of the selected teeth. Alternatively, a portion of the matrix inner surface may be conformed to complement the lingual surface of selected teeth. A stabilization member extends from the outer shell and includes an inside surface contoured to complement at least a portion of the facial surface of a tooth located adjacent the selected teeth. Orthodontic appliances are detachably connected to the matrix, wherein each appliance includes a base for bonding the appliance to a tooth.

DETAILED DESCRIPTION OF THE PREFERRED EMBODIMENT

Figure 1:
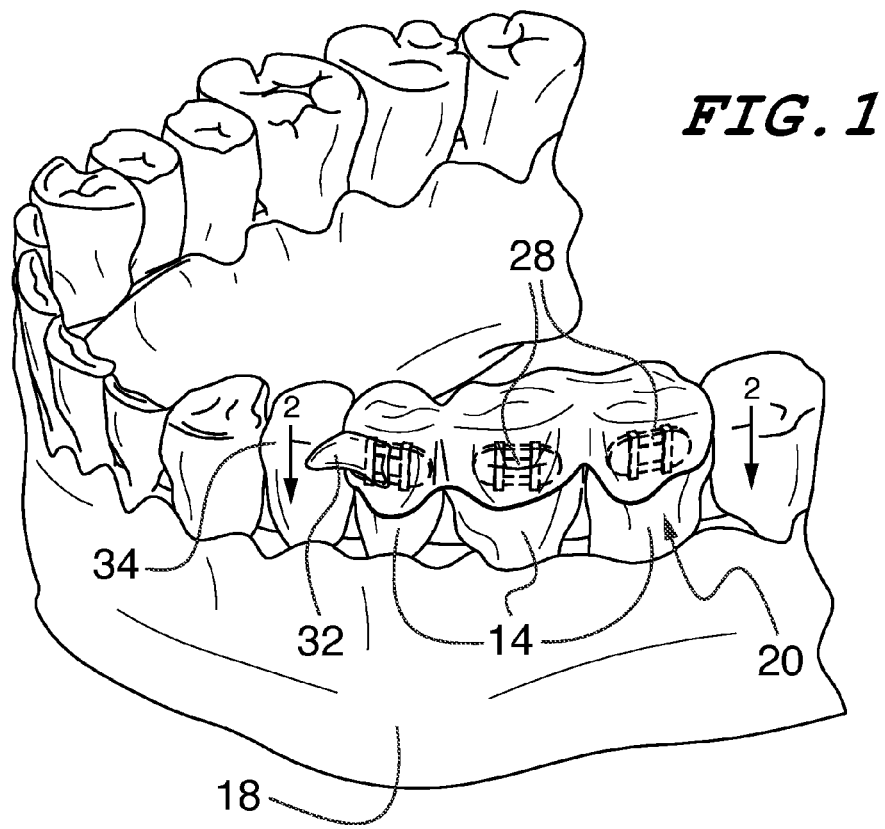
FIG. 1 is an isometric view of the orthodontic indirect bonding tray including stabilization features of the present invention applied to teeth of the upper dental arch of a patient, the upper dental arch being rotated one-hundred eighty degrees to illustrate the occlusal surfaces of the teeth located therein.
Figure 2:
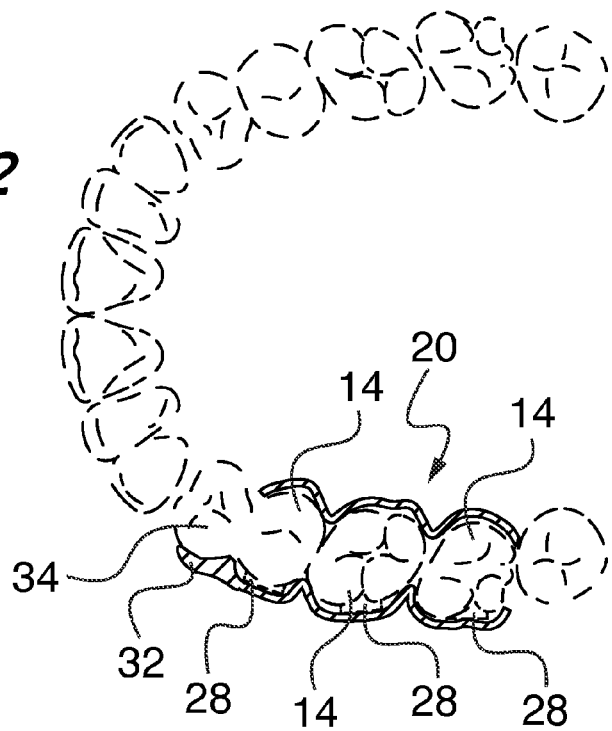
FIG. 2 is a view of the upper dental arch of FIG. 1 including a cross-sectional view of the orthodontic indirect bonding tray of the present invention, showing teeth in phantom.
Figure 3:
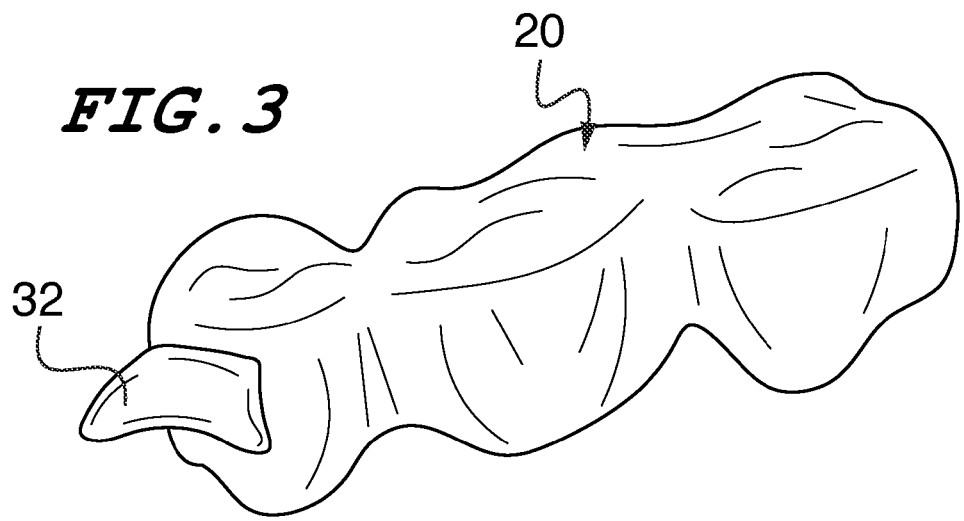
FIG. 3 is a perspective view of the orthodontic indirect bonding tray including stabilization features of the present invention.
Figure 4:
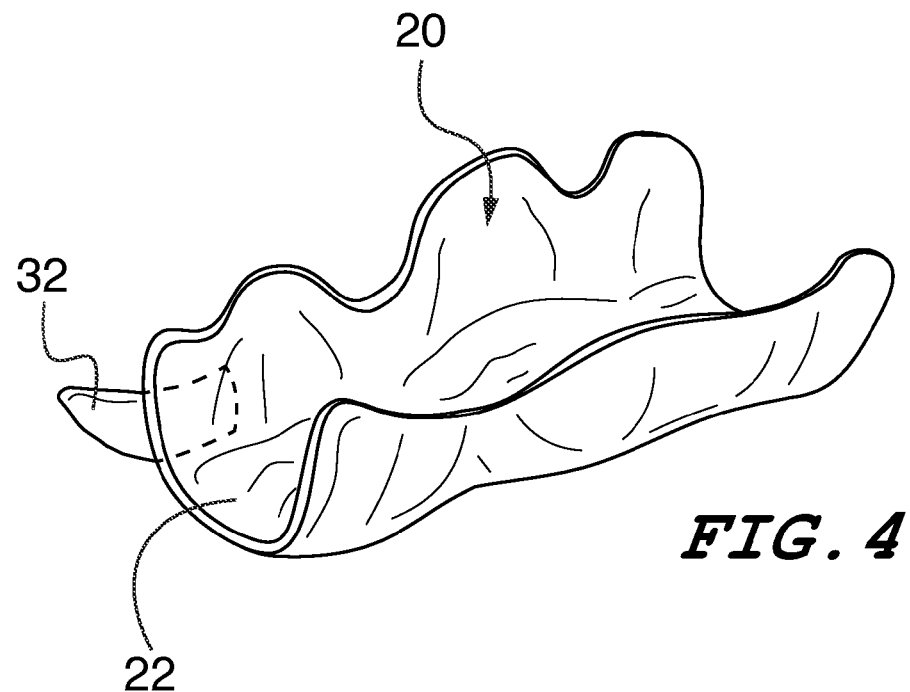
FIG. 4 is another isometric view of the orthodontic indirect bonding tray including stabilization features of the present invention; and, FIG. 5 is a cross-sectional view of the orthodontic indirect bonding tray including stabilization features of the present invention, shown mounted over teeth.

Referring now in greater detail to the drawings in which like numerals represent like components throughout the several views, there is shown in FIGS. 1-5 an embodiment of the orthodontic indirect bonding tray including stabilization features of the present invention which is broadly designated by the numeral 20. As best shown in FIGS. 1 and 2, the bonding tray 20 is shown positioned over several teeth 14 of the upper jaw 18, or maxilla, of an orthodontic patient, the teeth 14 requiring corrective orthodontic alignment. FIG. 1 illustrates the upper dental arch rotated one-hundred eighty degrees to illustrate the occlusal surfaces of the teeth located therein. Although the figures illustrate the indirect bonding tray of the present invention positioned over teeth of the upper jaw, it should be understood that it is within the scope of the present invention that the bonding tray 20 could be positioned over teeth of the lower jaw.

The tray 20 includes a channel 22 (FIG. 4) comprising a plurality, e.g. three, tooth cavities for receiving selected teeth 14 within a patient's dental arch. In the exemplary tray 20 shown in the drawings, the channel 22 is adapted to receive teeth 14 located in a patient's upper dental arch, although it should be understood in this regard that as an alternative, the tray 20 may be constructed to receive teeth 14 located in the patient's lower dental arch (not shown).

The tray 20 also includes a number of orthodontic appliances 28 that are detachably connected to the tray 20. In FIGS. 1-5, the exemplary illustrated orthodontic appliance 28 is an orthodontic bracket, although other appliances are also possible. Examples of other suitable appliances include buccal tubes, buttons, formed "bumps" made, e.g., of composite material, or any other metal or non-metal "handle" or other structure connected to the teeth 14 that provides an attachment point for a force member such as a wire, aligner tray, polymeric strip, elastomeric band or chain, or any combination of the foregoing.

Figure 5:
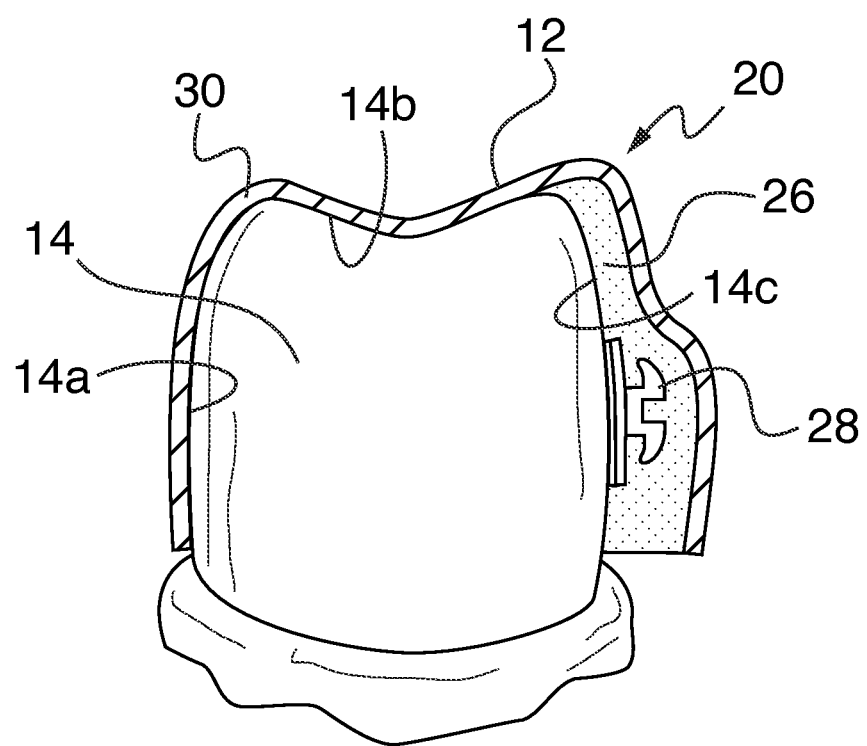

Referring now to FIG. 5, the tray 20 may be constructed according to any one of a variety of known techniques. In the example shown in FIG. 5, the tray 20 is formed of an inner matrix 26, formed of a relatively flexible material, and an outer shell 30, which is formed of a material that is relatively hard in comparison to the inner matrix 26.

The inner matrix 26 has a relatively low viscosity before hardening so that intimate contact between the inner matrix 26 and each appliance 28, e.g., orthodontic bracket, is assured. As best shown in FIGS. 1, 2 and 5, three appliances 28 are shown to be in contact with the inner matrix 26, although it should be understood in this regard that as an alternative, the tray 20 may be constructed to receive a greater or fewer number of appliances 28. As best shown in FIG. 5, the relatively soft inner matrix 26 is shown as penetrating the various recesses, cavities and other structural features of each appliance 28 so that a secure connection between the appliances 28 and the inner matrix 26 can be established. In FIG. 5, the inner matrix 26 is shown as contacting the facial surface of the tooth 14. The inner matrix 26 also includes a contour that matches and makes contact with the facial surface 14c of the patient's teeth 14 in the area surrounding the appliance 28.

It should be understood that alternatively, in the event appliances 28 are to be attached to the lingual surface of teeth 14, then the inner matrix 26 could be contoured to match and arranged to contact the lingual surface 14a of the teeth 14, as opposed to the facial surface. In other words, depending upon whether appliances 28 are to be attached to the facial 14c or lingual 14a surfaces of teeth 14 will dictate whether the inner matrix 26 is to be located adjacent the facial or lingual surface of the teeth 14. Any suitable material may be utilized for the inner matrix 26 so long as it is relatively clear to permit a curing light to pass through the inner matrix 26 to enable curing of the adhesive for bonding the appliances 28 to the surfaces of the teeth 14. An example of a suitable material for the inner matrix 26 is Essix® Bleach Tray and Model Duplication Material (1.5 mm thickness) available from Dentsply Raintree Essix, located in Metarie, La.

The relatively hard outer shell 30 includes a contour that precisely matches the surfaces of the tooth 14 where the outer shell 30 contacts the tooth 14, e.g., the lingual 14a and occlusal 14b surfaces of the tooth 14. For example, as shown in FIG. 5, the outer shell 30 directly contacts the lingual 14a and occlusal 14b surfaces, as well as surrounds the inner matrix 26 over the facial surface 14c of the patient's teeth 14. As shown in FIG. 5, the inner matrix 26 directly contacts the facial 14c surface of the tooth 14. Although not shown in the drawings, in the event appliances 28 are to be attached to the lingual surface 14a of teeth 14, then the outer shell 30 would include a contour that precisely matches the facial 14c and occlusal 14b surfaces of the tooth 14, and the outer shell would directly contact those tooth surfaces. The outer shell 30 would surround the inner matrix 26 over the lingual surface 14a of the patient's teeth 14, the inner matrix 26 being in direct contact with this tooth surface.

Preferably, the outer shell 30 chemically bonds to the inner matrix 26 with a relatively high bond strength. Any suitable material may be utilized for the outer shell 30 so long as it is relatively clear to permit a curing light to pass through the outer shell 30 to enable curing of the adhesive for attaching the appliances 28 to the surfaces of the teeth 14. An example of a suitable material for the relatively hard outer shell 30 is Essix A+® Plastic, also available from Dentsply Raintree Essix, located in Metarie, La.

For example, the relatively hard surface of the outer shell 30 directly contacts the patient's teeth on the lingual 14a and occlusal 14b surfaces of the teeth 14, while the relatively soft and flexible surface of the inner matrix 26 is limited to direct contact with the facial surface 14c of the teeth in the vicinity where it penetrates the appliances 28. By maximizing the amount of relatively hard outer shell 30 directly contacting the teeth 14 and minimizing the amount of relatively soft and flexible inner matrix 26 directly contacting the teeth 14, an improved mating fit of the tray 20 with the patient's teeth 14 may be obtained such that little, if any, tolerance or "slop" is present and relative movement between the tray 20 and the teeth 14 of the dental arch is substantially eliminated. In this manner, the transfer tray 20 is sufficiently rigid in the areas where it makes direct contact with the teeth 14. Such a construction will reduce instability, "wiggle", or "play" that often arises when the transfer tray is placed over matching surfaces of the patient's teeth during the indirect bonding process. In this manner, heightened assurance is provided to the practitioner that each appliance 28 will be positioned on the patient's teeth at precisely the same location that corresponds to the previous location of the same appliance on the stone model.

Moreover, as an additional feature to address the problem of inaccurate placement of the orthodontic appliance onto a patient's tooth, the tray 20 of the present invention is provided with a stabilization member 32 which is shown in FIGS. 1-4 as extending in the mesial direction from the anterior end of the tray 20 to a tooth 34 located adjacent the teeth 14 to which appliances 28 are to be applied. Although FIGS. 1-4 illustrate the stabilization member 32 extending in a mesial direction from the anterior end of the tray 20, it should be understood that the stabilization member 32 may extend in the distal direction from the posterior end of the tray 20 to an adjacent tooth 34, also for the purpose of increasing the accuracy of placement of the orthodontic appliance onto a patient's tooth 14. The stabilization member 32 provides an extra point of contact to adjacent structure, e.g. an adjacent tooth 34, and also provides a visual confirmation to the practitioner that a correct fit of the tray 20 that was originally planned for has been achieved. Such visual confirmation is especially important in cases where the tray 20 is arranged for placement over posterior teeth where the practitioner may have difficulty seeing the precise position of the bracket 28 relative to the tooth surface.

The inner surface of the stabilization member 32 is precisely contoured to the surface of the adjacent tooth 34 and provides a visual indicator of correct tray placement. As best shown in FIGS. 1 and 2, the stabilization member 32 is precisely contoured to match and positioned to contact the facial surface of the adjacent tooth 34. Although FIGS. 1 and 2 illustrate the stabilization member 32 as being positioned and contoured to contact the facial surface of the adjacent tooth, it should be understood that the stabilization member 32 may also be precisely contoured to match and positioned to contact the occlusal surface, or the lingual surface of the adjacent tooth 34. Alternatively, the stabilization member 32 could be positioned and contoured to contact two surfaces of the adjacent tooth, e.g., the facial and occlusal surfaces, or the lingual and occlusal surfaces of the adjacent tooth 34.

The stabilization member 32 may be formed of any suitable material, e.g., acrylic, acetate, resin, plastic, metal, silicone, polyvinyl, or materials derived from stereolitographic processes, among others. The stabilization member 32 may also be formed of the material used to form the outer shell 30. The stabilization member 32 may be transparent or translucent. The stabilization member 32 may be integral with the tray 20, or a separate component that is attached to the tray 20, by any suitable means.

It is understood that the orthodontic indirect bonding tray including stabilization features of the present invention and its constituent parts described herein is an exemplary indication of a preferred embodiment of the invention, and is given by way of illustration only. In other words, the concept of the present invention may be readily applied to a variety of preferred embodiments, including those disclosed herein. While the invention has been described in detail and with reference to specific examples thereof, it will be apparent to one skilled in the art that various changes and modifications can be made therein without departing from the spirit and scope thereof.

We claim:

1. An indirect orthodontic appliance bonding system comprising:
   an indirect bonding tray, wherein the indirect bonding tray comprises:
      an anterior end;
      a posterior end;
      an outer shell, wherein the outer shell comprises:
         wall sections configured to extend over at least a portion of facial, lingual, and occlusal surfaces of selected teeth; and
         a channel disposed between the wall sections of the outer shell, wherein the channel comprises tooth cavities, wherein each of the tooth cavities are configured to receive a tooth of the selected teeth; and
      an inner matrix bonded to at least a portion of the an inner surface of the outer shell, wherein the inner matrix is softer than the outer shell, wherein the inner matrix is disposed between the outer shell and at least one of the facial or lingual surface of the selected teeth during use, and wherein the inner matrix at least partially penetrates at least a portion of an orthodontic appliance during use; and
   a stabilization member external to the indirect bonding tray, wherein the stabilization member comprises:
      an attachment end coupled to the indirect bonding tray such that at least a portion of the stabilization member at least partially overlaps the indirect bonding tray;
      a free end extending in a mesial direction from the tray;
      a portion, wherein the portion comprises a surface contoured to approximately match at least one of:
         at least part of the facial surface or
         at least part of the occlusal surface of one or more teeth adjacent to the selected teeth, and wherein the stabilization member does not contact the lingual surface of teeth adjacent to the selected teeth;
      wherein the stabilization member is configured to stabilize the indirect bonding tray by contacting one or more of the teeth adjacent to the selected teeth.

2. The indirect orthodontic appliance bonding system of claim 1 wherein the inner matrix comprises an inner surface configured to extend over at least a portion of the facial surface or the lingual surface of the selected teeth.

3. The indirect orthodontic appliance bonding system of claim 1 wherein the stabilization member comprises at least one of acrylic, acetate, resin, plastic, metal, silicone, or polyvinyl.

4. The indirect orthodontic appliance bonding system of claim 1 wherein the stabilization member is clear.

5. The indirect orthodontic appliance bonding system of claim 1 wherein the stabilization member contacts at least a portion of the facial surface of one or more teeth adjacent to the selected teeth, and wherein the stabilization member does not contact the occlusal surface of one or more teeth adjacent to the selected teeth.

6. The indirect orthodontic appliance bonding system of claim 1 wherein the inner matrix is configured to at least partially surround each orthodontic appliance to couple the orthodontic appliance to the indirect bonding tray.

7. The indirect orthodontic appliance bonding system of claim 1 wherein at least one of the orthodontic appliances comprises an occlusal side, a facial side, and a gingival side, and wherein the inner matrix is configured to contact the occlusal side, the facial side and the gingival side during use.

8. The indirect orthodontic appliance bonding system of claim 1 wherein the stabilization member contacts at least a portion of the occlusal surface of one or more teeth adjacent to the selected teeth, and wherein the stabilization member does not contact the facial surface of one or more teeth adjacent to the selected teeth.

9. The indirect orthodontic appliance bonding system of claim 1 wherein the outer shell is configured to contact the lingual and occlusal surfaces, and wherein the outer shell is configured to not contact the facial surface of the selected teeth, and wherein the inner matrix is configured to contact at least a portion of the facial surface of the selected teeth.

10. An indirect orthodontic appliance bonding system comprising:
    an indirect bonding tray, wherein the indirect bonding tray comprises:
       an anterior end;
       a posterior end;
       an outer shell, wherein the outer shell comprises:
          wall sections configured to extend over at least a portion of facial, lingual, and occlusal surfaces of selected teeth; and
          a channel disposed between the wall sections of the outer shell, wherein the channel comprises tooth cavities, wherein each of the tooth cavities are configured to receive a tooth of the selected teeth; and
       an inner matrix bonded to at least a portion of the an inner surface of the outer shell, wherein the inner matrix is softer than the outer shell, wherein the inner matrix is disposed between the outer shell and at least one of the facial or lingual surface of the selected teeth during use, and wherein the inner matrix at least partially penetrates at least a portion of an orthodontic appliance during use; and
    a stabilization member external to the indirect bonding tray, wherein the stabilization member comprises:
       an attachment end attached to the indirect bonding tray such that at least a portion of the stabilization member at least partially overlaps the indirect bonding tray;
       a free end extending in a mesial direction from the tray;
       a portion, wherein the portion comprises a surface contoured to approximately match at least a portion of the facial surface and at least a portion of the occlusal surface of one or more teeth adjacent to the selected teeth, and wherein the stabilization member does not contact the lingual surface of teeth adjacent to the selected teeth;
       wherein the stabilization member is configured to stabilize the indirect bonding tray by contacting one or more of the teeth adjacent to the selected teeth.

11. The indirect orthodontic appliance bonding system of claim 10 wherein the inner matrix comprises an inner surface configured to extend over at least a portion of the facial surface or the lingual surface of the selected teeth.

12. The indirect orthodontic appliance bonding system of claim 10 wherein the stabilization member comprises at least one of acrylic, acetate, resin, plastic, metal, silicone, or polyvinyl.

13. The indirect orthodontic appliance bonding system of claim 10 wherein the stabilization member is clear.

14. The indirect orthodontic appliance bonding system of claim 10 wherein the inner matrix allows curing light through the inner matrix to allow bonding material coupled to an orthodontic appliance disposed in the inner matrix to cure.

15. The indirect orthodontic appliance bonding system of claim 10 the outer shell is configured to contact the lingual and occlusal surfaces, and wherein the outer shell is configured to not contact the facial surface of the selected teeth, and wherein the inner matrix is configured to contact at least a portion of the facial surface of the selected teeth.

16. The indirect orthodontic appliance bonding system of claim 10 wherein the inner matrix is configured to at least partially surround each orthodontic appliance to couple the orthodontic appliance to the indirect bonding tray.

17. A method of applying a set of orthodontic appliances to selected teeth, wherein the method comprises:
   positioning a set of orthodontic appliances in an indirect bonding tray, wherein the indirect bonding tray includes an outer shell and an inner matrix coupled to at least a portion of a channel in the outer shell;
   allowing the inner matrix to penetrate at least a portion of each of the orthodontic appliances in the set of orthodontic appliances;
   positioning the indirect bonding tray in a patient's mouth such that the inner matrix contacts the facial surface of the selected teeth and a stabilization member contacts one or more teeth adjacent to the selected teeth, wherein the stabilization member is external to the indirect bonding tray, and wherein the stabilization member is coupled to the indirect bonding tray such that at least a portion of the stabilization member at least partially overlaps the indirect bonding tray; and
   allowing a bonding material coupled to the set of orthodontic appliances to cure, wherein the curing of the bonding material secures the set of orthodontic appliances to the selected teeth.

18. The method of claim 17 wherein the set of orthodontic appliances are detachably connected to the inner matrix.

19. The method of claim 17 wherein positioning the indirect bonding tray in a patient's mouth allows the outer shell to contact at least a portion of the selected teeth.

* * * * *